US011058731B2

(12) United States Patent
Kuchina

(10) Patent No.: US 11,058,731 B2
(45) Date of Patent: *Jul. 13, 2021

(54) TOPICAL HALOBACTERIA EXTRACT COMPOSITION FOR TREATING RADIATION SKIN TISSUE DAMAGE

(71) Applicant: DR. NONA INTERNATIONAL LTD., Rishon Lezion (IL)

(72) Inventor: Nona Kuchina, Rishon Lezion (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/796,897

(22) Filed: Oct. 30, 2017

(65) Prior Publication Data

US 2018/0042971 A1 Feb. 15, 2018

Related U.S. Application Data

(63) Continuation of application No. 14/666,790, filed on Mar. 24, 2015, which is a continuation-in-part of application No. PCT/IL2013/050786, filed on Sep. 16, 2013.

(60) Provisional application No. 61/086,657, filed on Oct. 2, 2012.

(30) Foreign Application Priority Data

Sep. 24, 2012 (IL) .......................................... 222127

(51) Int. Cl.
| | | |
|---|---|---|
| *A61K 35/74* | (2015.01) | |
| *A61K 9/08* | (2006.01) | |
| *A61K 9/00* | (2006.01) | |
| *A61K 36/05* | (2006.01) | |
| *A61K 8/99* | (2017.01) | |
| *A61Q 19/00* | (2006.01) | |
| *A61K 9/06* | (2006.01) | |

(52) U.S. Cl.
CPC ................ *A61K 35/74* (2013.01); *A61K 8/99* (2013.01); *A61K 9/0014* (2013.01); *A61K 9/06* (2013.01); *A61K 9/08* (2013.01); *A61K 36/05* (2013.01); *A61Q 19/004* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 5,536,419 A | 7/1996 | Escalona et al. | |
| 5,948,823 A | 9/1999 | Ben-Amotz et al. | |
| 6,248,340 B1 * | 6/2001 | Maor | A61K 8/965 424/195.17 |
| 2003/0017973 A1 * | 1/2003 | Rodelet | A61K 8/64 514/18.8 |
| 2015/0202236 A1 | 7/2015 | Kuchina | |
| 2015/0202237 A1 | 7/2015 | Kuchina | |

FOREIGN PATENT DOCUMENTS

| | | |
|---|---|---|
| EP | 1250918 A1 | 10/2002 |
| IL | 222127 | 3/2013 |
| IL | 222128 | 3/2013 |
| RU | 2109515 C1 | 4/1998 |
| WO | 2014/045279 A1 | 3/2014 |
| WO | 2014/045280 A1 | 3/2014 |

OTHER PUBLICATIONS

Restriction Requirement Office Action issued by the U.S. Patent and Trademark Office dated Apr. 12, 2017, for U.S. Appl. No. 14/666,823.
Gurevich P. et al, "Effect of homogenate from dead sea halobacteria on proliferation and survival of normal and tumor cells following treatment with ionizing radiation or H2O2", Jan. 2002, vol. 47, Issue 6, pp. 15-20, Dec. 31, 2002.
Kuchina N., "Dead Sea—the source of life and health", Sep. 23, 2005.
Response filed on Aug. 10, 2017 in reply to Restriction Requirement Office Action issued by the U.S. Patent and Trademark Office dated Apr. 12, 2017, for U.S. Appl. No. 14/666,823.
International Preliminary Report on Patentability (Chapter I) for PCT/IL2013/050785, dated Mar. 24, 2015.
International Preliminary Report on Patentability (Chapter I) for PCT/IL2013/050786, dated Mar. 24, 2015.
International Search Report for PCT/IL2013/050785, dated Dec. 31, 2013.
Written Opinion of the International Search Authority for PCT/IL2013/050786, dated Jan. 2, 2014.
Written Opinion of the International Search Authority for PCTIL2013050785, dated Dec. 31, 2013.
Oren A., "Diversity of halophilic microorganisms: Environments, phylogeny, physiology, and applications", Journal of Industrial Microbiology & Biotechnology, 2002, 28, 56-63, 2002 Nature Publishing Group, Dec. 31, 2002, pp. 56-63.

(Continued)

*Primary Examiner* — Thane Underdahl

(57) ABSTRACT

The present invention provides a composition for treating skin damage, comprising Halobacteria extracts and *Dunaliella* extracts. The aforementioned extracts further comprising strong antioxidants with high redox potential when dissolved in oil and in water. The strong antioxidants inhibiting in a known oxidative mechanisms which are further correlated with skin damage, wherein the Halobacteria extract is Archaebacteria DN-1 having a wide range impact on rehabilitation of the skin tissue after radiation, and wherein said Halobacteria extracts and *Dunaliella* extracts combination promotes rehabilitation of the skin tissue after radiation, and provides a synergistic effect on a mammalian skin. Furthermore, the composition is preferably adapted for topical delivery.

18 Claims, 8 Drawing Sheets

(56) References Cited

OTHER PUBLICATIONS

Non-Final Rejection Office Action issued by the U.S. Patent and Trademark Office dated Jul. 27, 2017, for U.S. Appl. No. 14/666,790.
Restriction Requirement Office Action issued by the U.S. Patent and Trademark Office dated Oct. 6, 2016, for U.S. Appl. No. 14/666,790.
Response filed on Jan. 4, 2017, in reply to Restriction Requirement Office Action issued by the U.S. Patent and Trademark Office dated Oct. 6, 2016, for U.S. Appl. No. 14/666,790.
Gvirtz, Raanan, et al. "Kinetic Cytokine Secretion Profile of LPS-Induced Inflammation in the Human Skin Organ Culture." Pharmaceutics, vol. 12, No. 4, 2020, p. 299., doi:10.3390/pharmaceutics12040299.
Yoshimura, A., Hara, Y., Kaneko, T., & Kato, I. (1997). Secretion of IL-1beta, TNF-alpha, IL-8 and IL-1ra by human polymorphonuclear leukocytes in response to lipopolysaccharides from periodontopathic bacteria. Journal of Periodontal Research, 32(3), 279-286. doi:10.1111/j.1600-0765.1997.tb00535.x.

\* cited by examiner

TOPICAL HALOBACTERIA EXTRACT COMPOSITION FOR TREATING RADIATION SKIN TISSUE DAMAGE

FIELD OF THE INVENTION

This invention is directed towards a composition for treating skin damage by using a combination of Halobacteria extracts and *Dunaliella* extracts. More specifically the invention relates to a composition comprising a combination of Halobacteria extracts and *Dunaliella* extracts for enhancement and rehabilitation of the skin tissue after radiation treatment.

BACKGROUND OF THE INVENTION

Halobacteria are known as halophilic microorganisms. This type of archaeon can act as a good model for some aspects of eukaryotic biology, such as DNA replication, transcription, and translation. Comparing a halophile genome to that of other prokaryotes should give insight into microbial adaptation to extreme conditions.

Halobacteria are extreme obligate bacteria. They require, for their growth, very high salt concentrations (from 10 to 30%), KCl, MgCl2 and especially NaCl. These organisms are isolated from natural media. To maintain their internal osmotic pressure which should be in equilibrium with the NaCl concentration in the medium, Halobacteria accumulate from 3 to 4 M of salt in their cytoplasm in the form of KCl. A suspension of Halobacteria in a medium containing a NaCl concentration of 2M causes complete loss of the stiffness of the bacterial envelope and the bacterium then assumes a round shape. Decreasing the salt concentration below 1 M leads to bacterial lysis. Colonies of Halobacteria are red in color, their envelopes indeed contain colored pigments (bacterio-ruberins) which protect them against intense ultraviolet radiation to which they are exposed. Halobacteria possess a pigment, halorhodopsin, which pumps chloride ions in the cell in response to photons, creating a voltage gradient and assisting in the production of energy from light. The process is unrelated to other forms of photosynthesis involving electron transport however, and Halobacteria are incapable of fixing carbon from carbon dioxide.

The conventional shape of *Halobacterium* in a salt-rich medium is that of an oblong *bacillus* 4 to 10 [mu]m long and 0.7 [mu]m in diameter. This bacterium possesses from 5 to 8 lophotrichous flagella. *Halobacterium halobium* is incapable of using carbohydrates as carbon and energy source.

EP application no. 1250918 discloses extraction process and the use of a glycoprotein fraction extracted from an archaebacterium: *Halobacterium halobium*.

The product described, incorporated into a cosmetic preparation, has the peculiarity to protect skin cells from the harmful effects of pollution and/or radiation.

RU application no. 2109515 discloses a strain *Halobacterium halobium* preparation showing bioactive properties. This strain produces the broad spectrum of biological macrobiotic activity. Antiradical effect of preparation stops destructive effect of labile free radicals. Preparation is a lyophilized powder of *Halobacterium* biomass and can be used as a biologically active addition to food, as an agent decreasing toxic effect of antitumor compounds. Preparation can be used for prophylaxis and therapy of radiation sickness.

A variety of Halobacteria extracts are known to have advantageous cosmetic and/or therapeutic properties especially for the treatment of scars, thermal, electrical chemical and sun burns or different types of sores as topical composition such as milk, cream, lotion, serum, mask or gel.

There thus remains an unmet and long felt need to provide means and methods for improved treatment of skin tissue burns, blemishes and defects.

SUMMARY OF THE INVENTION

It is one object of the present invention to provide a topical composition for treating skin damage comprising: (a) Halobacteria extracts comprising strong antioxidants with high redox potential; said strong antioxidants inhibiting known oxidative mechanisms correlated with skin damage; and (b) *Dunaliella* extracts for reducing the amount of free radicals in skin damage;

wherein said topical composition has synergistic anti-inflammatory effect, defined by attenuation of at least of Il-1β or TNF-α induction on said inflamed skin as compared to an untreated control skin.

It is another object of the present invention to provide the composition as defined above, wherein said Halobacteria extract is Halobacteria homogenate, Archaebacteria DN1, and said Archaebacteria DN-1 has an anti-oxidant activity substantially correlated with a body serum total antioxidant capacity (TAC) of at least 167.1 μMol Trolox Equivalent/ 100 g; said anti-oxidant activity measured at the treatment site by at least one assay selected from a group consisting of:
  i. Assay 1—oxygen radical absorbent capacity (ORAC);
  ii. Assay 2—of ferric reducing ability of plasma (FRAP);
  iii. Assay 3—of 2,2-diphenyl-1-picrylhydrazyl (DPPH);
  iv. Assay 4—of 3-ethyl-benzothiazoline-6-sulfonic acid (ABTS);
  v. Assay 5—of Trolox Equivalent Antioxidant Capacity (TEAC); and
    any combination thereof.

It is another object of the present invention to provide the composition as defined above, wherein said body serum measurement is taken from any body site.

It is another object of the present invention to provide the composition as defined above wherein said Assays 1-5 measurement of total antioxidant activity is performed in a serum sample of said composition.

It is another object of the present invention to provide the composition as defined above, wherein said Halobacteria extracts configured to actuate: (a) antioxidant and redox potential to a wound site, correlated with an increase in erythrocytes (RBC), leukocytes (WBC), Interleukin-6 (IL-6) concentration and glutathione concentration in a treated subject compared with an untreated control; and (b) protection of membranes from oxidation by reacting with radicals produced in the chain reaction.

It is another object of the present invention to provide the composition as defined above, wherein said composition is configured to affect one selected from a group consisting of: (a) decreasing of clinical syndromes resulting from radiation in variety of systems such as the nerve system, digesting system and vascular system; and (b) treating cardiac, liver or vascular diseases, stabilization and improvement of the immune system and the endocrine system; and any combination thereof.

It is another object of the present invention to provide the composition as defined above, wherein said composition comprises by weight, 10%-2.5% Archaebacteria DN-1.

It is another object of the present invention to provide the composition as defined above, wherein said topical composition is selected from the group consisting of: a gel, a milk, a lotion, a serum, a mask, ointments or a cream.

It is another object of the present invention to provide the composition as defined above, wherein said skin damage is selected from the group consisting of: skin blemish, scars, burns, mucositis or/and bedsores resulting from radiation treatment, surgery or any drug treatment.

It is another object of the present invention to provide the composition as defined above, wherein said composition promotes rehabilitation of the body tissue after radiation comprising at least one selected from a group consisting of alleviation of depression, reduction of clinical syndromes resulting from radiation, treatment of cardiac, liver or vascular diseases, stabilization and improvement of the immune system and the endocrine system and any combination thereof.

It is another object of the present invention to provide the composition as defined above, wherein said composition further comprises preservatives, surfactants, humectants, emulsifiers, thickening agents, perfumes, preservatives, vegetable or mineral oils, antiseptic agents, acidifying or alkalinizing agents, vitamins, anti-UV agents, solvents, pH-stabilizing agents, silicones and combination thereof.

It is one object of the present invention to provide a method of producing a topical composition for treating skin damage comprising the steps of: (a) obtaining Halobacteria extracts comprising strong antioxidants with high redox potential; said strong antioxidants inhibiting known oxidative mechanisms correlated with skin damage; (b) obtaining *Dunaliella* extracts for reducing the amount of free radicals in skin damage; and (c) mixing said Halobacteria extracts and *Dunaliella* extracts;

wherein said topical composition has synergistic anti-inflammatory effect, defined by attenuation of at least of Il-1β or TNF-α induction on said inflamed skin as compared to an untreated control skin.

It is another object of the present invention to provide the method as defined above, wherein said Halobacteria extract is Halobacteria homogenate, Archaebacteria DN1, and producing of said Archaebacteria DN1 comprising the steps of: (a) obtaining a bacterial mass by culturing Halobacteria; (b) dispersing a quantity of the bacterial mass in a salt solution solvent to form a solution; (c) incubating the solution for about 2 weeks at about 42° C.; (d) centrifuging solution of (c), yielding a sediment; (e) re-suspending isolated sediment layer of (d) to form a solution (f) repeating (d) and (e) twice to form a solution; (g) sonicating solution of (f) three times; (h) centrifuging of sonicated solution of (g), yielding a sediment wherein said sediment of (h), Halobacteria homogenate, is Archaebacteria DN1, having an anti-oxidant activity which has a wide range impact on rehabilitation of the skin tissue after radiation; said activity substantially correlated with a body serum TAC of at least 167.1 µMol Trolox Equivalent/100 g at the treatment site; said anti-oxidant activity measured at the treatment site by at least one assay selected from a group consisting of:
 i. Assay 1—oxygen radical absorbent capacity (ORAC);
 ii. Assay 2—of ferric reducing ability of plasma (FRAP);
 iii. Assay 3—of 2,2-diphenyl-1-picrylhydrazyl (DPPH);
 iv. Assay 4—of 3-ethyl-benzothiazoline-6-sulfonic acid (ABTS);
 v. Assay 5—of Trolox Equivalent Antioxidant Capacity (TEAC); and
  any combination thereof.

It is another object of the present invention to provide the method as defined above, wherein said solvent comprises salt solution and at least one of a group comprising peptone, yeast extract, casein, and any combination thereof.

It is another object of the present invention to provide the method as defined above, wherein said composition is for one selected from a group consisting of: (a) decreasing of clinical syndromes resulting from radiation in variety of systems such as the nerve system, digesting system and vascular system; (b) treating cardiac, liver or vascular diseases, stabilization and improvement of the immune system and the endocrine system; and any combination thereof.

It is another object of the present invention to provide the method as defined above, wherein said composition comprises:
 i. by weight, 10%-2.5% Archaebacteria DN-1;
 ii. preservatives, surfactants, humectants, emulsifiers, thickening agents, perfumes, preservatives, vegetable or mineral oils, antiseptic agents, acidifying or alkalinizing agents, vitamins, anti-UV agents, solvents, pH-stabilizing agents, silicones; and any combination thereof.

It is another object of the present invention to provide the method as defined above, wherein the composition: (a) treats skin blemish such as scars, burns or/and bedsores resulting from radiation, surgery or any drug treatment; (b) promotes rehabilitation of the body tissue after radiation, alleviation of depression, reduction of clinical syndromes resulting from radiation, treatment of cardiac, liver or vascular diseases, stabilization and improvement of the immune system and the endocrine system; and any combination thereof.

It is another object of the present invention to provide the method as defined above, wherein said Halobacteria extract has antioxidant activity due to its redox properties, resulting in increment of erythrocytes (RBC), leukocytes (WBC), Interleukin-6 (IL-6) concentration and glutathione concentration.

BRIEF DESCRIPTION OF THE FIGURES

In order to understand the invention and to see how it may be implemented in practice, a plurality of embodiments is adapted to now be described, by way of non-limiting example only, with reference to the accompanying drawings, wherein.

DETAILED DESCRIPTION

Figure 1:
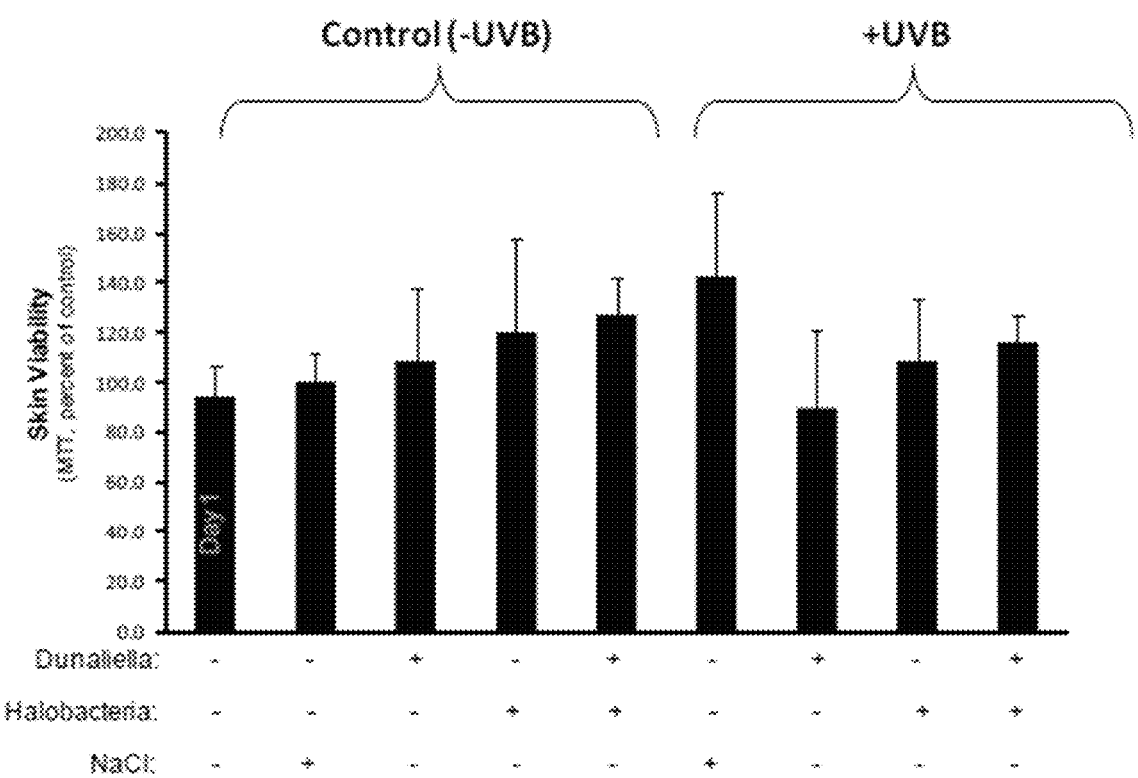
FIG. 1 presents a graph of MTT assay results of the different treatment groups without or with UVB radiation, in accordance with a preferred embodiment of the present invention. The Human Skin Organ Cultures (HSOC) were incubated without or with 20% *Dunaliella* (0.69 mg/cm$^2$) or halobacteria (2.76 mg/cm$^2$) or both for 24 hr and exposed to 300 mJ UVB irradiation. Then, epidermis viability was measured by MTT assay. Results are shown as percent of control. Mean±SEM, n=3,4. Results show that the different extracts did not comprise human skin viability.

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide an archaebacteria DN-1 useful for treating skin damages resulting from radiation, surgery or any drug treatment (such as scars, burns, bedsores and mucositis).

The present invention is a composition which includes Archaebacteria DN-1 which comprises strong antioxidants that dissolved in oil and in water. The composition has a wide range impact on rehabilitation of the skin. The treatment is delivered topically. Treatment with Archaebacteria DN-1 comprising strong antioxidants prevents propagation of tissue damage and improve both survival and neurological outcome of diseases. One of the parameters that is modulated either by radical overload or by intake of dietary antioxidants (and can therefore be regarded as more representative of the in vivo balance between oxidizing species and antioxidant compounds unknown, measurable and not measurable) is plasma total antioxidant capacity (TAC).

There are several methods to assess the antioxidant activity of a substance:

Assay 1—Oxygen radical absorbance capacity (ORAC) is a method of measuring antioxidant capacities in biological samples in vitro. The assay measures the oxidative degradation of the fluorescent molecule (either beta-phycoerythrin or fluorescein) after being mixed with free radical generators such as azo-initiator compounds.

Assay 2—The antioxidant activity can also be measured by ferric reducing antioxidant power (FRAP) assay. Ferric reducing ability of plasma (FRAP, also Ferric ion reducing antioxidant power) is an antioxidant capacity assays which uses Trolox as a standard FRAP assay uses antioxidants as reluctant in a redox-linked colorimetric method, employing an easily reduced oxidant system presenting stoichiometric excess.

Assay 3—DPPH (2-diphenyl-1-picrylhydrazyl) is composed of stable free-radical molecules. DPPH acts as a monitor of chemical reactions involving radicals. DPPH is radical and a trap ("scavenger") for other radicals. Therefore, rate reduction of a chemical reaction upon addition of DPPH is used as an indicator of the radical nature of a reaction. The DPPH assay provides an easy and rapid way to evaluate potential antioxidants.

Assay 4-ABTS (2,2'-azino-bis(3-ethylbenzothiazoline-6-sulphonic acid) assay is another method to measure antioxidant capacities. In this assay, ABTS is converted to its radical cation by addition of sodium persulfate. This radical cation is blue in color and absorbs light at 734 nm. The ABTS radical cation is reactive towards most antioxidants including phenolics, thiols and Vitamin C. During this reaction, the blue ABTS radical cation is converted back to its colorless neutral form. The reaction may be monitored spectrophotometrically. This assay is often referred to as the Trolox equivalent antioxidant capacity (TEAC) assay. The reactivity of the various antioxidants tested are compared to that of Trolox, which is a water-soluble analog of vitamin E.

Assay 5-Trolox equivalent antioxidant capacity (TEAC) is an additional measurement of antioxidant strength based on Trolox, measured in units called Trolox Equivalents (TE), e.g. μmolTE/100 g. Due to the difficulties in measuring individual antioxidant components of a complex mixture (such as blueberries or tomatoes), Trolox equivalency is used as a benchmark for the antioxidant capacity of such a mixture. Trolox equivalency is most often measured using the ABTS decolorization assay.

The present invention further provides a composition for treating skin damages in a mammalian subject the composition comprising a Archaebacteria DN-1 a Halobacterial extract, the extract comprising: (a) at least one water soluble fraction; and (b) at least one oil soluble fraction. The Archaebacteria DN-1 provides an anti oxidant activity as measured by any of in vitro Assays 1-5; the activity substantially correlated with a body serum total antioxidant capacity (TAC) of at least 167.1 μMolTE/100 g measured by oxygen radical absorbent capacity (ORAC) Assay 1 at the treatment site.

The present invention further provides a composition for treating skin damages in a mammalian subject the composition comprising a Archaebacteria DN-1 Halobacteria extract the extract comprising: (a) at least one water soluble fraction; and (b) at least one oil soluble fraction. The Archaebacteria DN-1 provides an anti-oxidant activity as measured by any of in vitro Assay 1-5; the activity substantially correlated with a body serum TAC of at least 167.1 μMolTE/100 g measured by ferric reducing ability of plasma (FRAP) Assay 2 at the treatment site.

The present invention further provides a composition for treating skin damages in a mammalian subject the composition comprising a Archaebacteria DN-1 Halobacteria extract the extract comprising: (a) at least one water soluble fraction; and (b) at least one oil soluble fraction. The Archaebacteria DN-1 provides an anti oxidant activity as measured by any of in vitro assay 1-4; the activity substantially correlated with a body serum TAC of at least 167.1 μMolTE/100 g measured by 2,2-diphenyl-1-picrylhydrazyl (DPPH) Assay 3 at the treatment site.

The present invention further provides a composition for treating skin damages in a mammalian subject the composition comprising a Archaebacteria DN-1 Halobacterial extract the extract comprising: (a) at least one water soluble fraction; and (b) at least one oil soluble fraction. The Archaebacteria DN-1 provides an anti-oxidant activity as measured by any of in vitro assay 1-4; the activity substantially correlated with a body serum TAC of at least 167.1 μMolTE/100 g measured by 3-ethyl-benzothiazoline-6-sulfonic acid (ABTS) Assay 4 at the treatment site.

The present invention further provides a composition for treating skin damages in a mammalian subject the composition comprising a Archaebacteria DN-1 Halobacterial extract the extract comprising: (a) at least one water soluble fraction; and (b) at least one oil soluble fraction. The Archaebacteria DN-1 provides an anti oxidant activity as measured by any of in vitro assay 1-4; the activity substantially correlated with a body serum TAC of at least 167.1 μMolTE/100 g measured by Trolox Equivalent Antioxidant Capacity (TEAC) Assay 5 at the treatment site.

The body serum measurement is taken form any body site. The serum total antioxidant capacity is expressed in mM Trolox equivalents.

Halobacteria extract has potential applications as strong antioxidants which dissolved in oil and in water; the strong antioxidants have a capacity to inhibit oxidative mechanisms that leads to skin damages.

The Halobacteria extract has antioxidant activity due to its redox properties, resulting in increment of erythrocytes (RBC), leukocytes (WBC), Interleukin-6 (IL-6) concentration and glutathione concentration.

The increment of IL-6 a pro-inflammatory and anti-inflammatory cytokine secreted by T cells and macrophages, stimulates immune response, during infection and after trauma.

The Halobacteria extract further protects membranes from oxidation by reacting with radicals produced in the chain reaction.

The present invention may provide Halobacteria extracts based food supplements, pharmaceuticals, nutraceuticals, cosmeceuticals, dressings and other extract based products directed to scars, burns or different types of sores and more particularly rehabilitation of the body tissue after radiation, alleviation of depression, both topically and orally.

Several uses and benefits of the compositions may also be included such as: Decreasing of clinical syndromes resulting from radiation in variety of systems (such as the nerve system, digesting system and vascular system). Treating patient suffering from cardiac, liver or vascular diseases with Halobacteria compositions. Stabilization and improvement of the immune system and also the endocrine system are also made possible by some embodiments of the present invention.

The term "Halobacteria", "Archaebacteria", "halophilic archaea Halobacteria" as used herein should be further understood also as Archaebacterium, *Halobacterium halobium*. Several side effects resulting from radiation therapy are usually limited to the area of the patient's body that is under treatment. One of the aims of radiation therapy is to reduce side effects to a minimum.

The main side effects reported are fatigue and skin irritation, such as a mild to moderate burn. The fatigue often sets in during the middle of a course of treatment and can last for weeks after treatment ends. The irritated skin will heal, but may not be as elastic as it was before.

There several Acute side effects resulting from radiation treatment.

Damage to the epithelial surfaces;

Epithelial surfaces may sustain damage from radiation therapy. Depending on the area being treated, this may include the skin, oral mucosa, pharyngeal, bowel mucosa and ureter. The rates of onset of damage and recovery from it depend upon the turnover rate of epithelial cells. Typically the skin starts to become pink and sore several weeks into treatment. The reaction may become more severe during the treatment and for up to about one week following the end of radiation therapy, and the skin may break down.

Although this moist desquamation is uncomfortable, recovery is usually quick. Skin reactions tend to be worse in areas where there are natural folds in the skin, such as underneath the female breast, behind the ear, and in the groin.

Mouth and throat sores;

If the head and neck area is treated, temporary soreness and ulceration commonly occur in the mouth and throat. If severe, this can affect swallowing, and the patient may need painkillers and nutritional support/food supplements. The esophagus can also become sore if it is treated directly, or if, as commonly occurs, it receives a dose of collateral radiation during treatment of lung cancer.

Late side effects occur months to years after treatment and are generally limited to the area that has been treated. They are often due to damage of blood vessels and connective tissue cells. Many late effects are reduced by fractionating treatment into smaller parts.

Fibrosis;

Tissues which have been irradiated tend to become less elastic over time due to a diffuse scarring process.

Epilation;

Epilation (hair loss) may occur on any hair bearing skin with doses above 1 Gy. It only occurs within the radiation field/s. Hair loss may be permanent with a single dose of 10 Gy, but if the dose is fractionated permanent hair loss may not occur until dose exceeds 45 Gy.

Dryness;

The salivary glands and tear glands have a radiation tolerance of about 30 Gy in 2 Gy fractions, a dose which is exceeded by most radical head and neck cancer treatments. Dry mouth (xerostomia) and dry eyes (xerophthalmia) can become irritating long-term problems and severely reduce the patient's quality of life. Similarly, sweat glands in treated skin (such as the armpit) tend to stop working, and the naturally moist vaginal mucosa is often dry following pelvic irradiation.

Lymphedema, a condition of localized fluid retention and tissue swelling, can result from damage to the lymphatic system sustained during radiation therapy. It is the most commonly reported complication in breast radiation therapy patients who receive adjuvant axillary radiotherapy following surgery to clear the axillary lymph nodes.

Heart disease;

Radiation has potentially excess risk of death from heart disease seen after some past breast cancer RT regimens.

Radiation proctitis;

This can involve long-term effects on the rectum including bleeding, diarrhea and urgency and is associated with radiation therapy to pelvic organs. Pelvic radiation therapy can also cause radiation cystitis when the bladder is affected One of the adverse effects of chemotherapy and radiotherapy treatment for cancer is mucositis, known as a painful inflammation and ulceration of the mucous membranes lining the digestive tract. Mucositis can occur anywhere along the gastrointestinal (GI) tract, but oral mucositis refers to the particular inflammation and ulceration that occurs in the mouth. Oral mucositis is a common and often debilitating complication of cancer treatment.

Oral and gastrointestinal (GI) mucositis affects almost all patients undergoing high-dose chemotherapy and hematopoietic stem cell transplantation (HSCT), 80% of patients with malignancies of the head and neck receiving radiotherapy, and a wide range of patients receiving chemotherapy. Alimentary tract mucositis increases mortality and morbidity and contributes to rising health care costs Radiotherapy to the head and neck or to the pelvis or abdomen is associated with Grade 3 and Grade 4 oral or GI mucositis, respectively, often exceeding 50% of patients. Among patients undergoing head and neck radiotherapy, pain and decreased oral function may persist long after the conclusion of therapy. Fractionated radiation dosage increases the risk of mucositis to >70% of patients in most trials. Oral mucositis is particularly profound and prolonged among HSCT recipients who receive total-body irradiation.

Cancer patients undergoing chemotherapy usually become symptomatic four to five days after beginning treatment, reaching a peak at around day 10, and then slowly improving over the course of a few weeks. Mucositis associated with radiotherapy usually appears at the end of the second week of treatment and may last for six to eight weeks. As a result of cell death in reaction to chemo- or radio-therapy, the mucosal lining of the mouth becomes thin, may slough off and then become red, inflamed and ulcerated. The ulcers may become covered by a yellowish white fibrin clot called a pseudomembrane. Peripheral erythema is usually present. Ulcers may range from 0.5 cm to greater than 4 cm. Oral mucositis can be severely painful. The degree of pain is usually related to the extent of the tissue damage. Pain is often described as a burning sensation accompanied by reddening.

Sores or ulcerations results from the radiation can become infected by virus, bacteria or fungus. Pain and loss of taste perception makes it more difficult to eat, which leads to weight loss. Ulcers may act as a site for local infection and a portal of entry for oral flora that, in some instances, may cause septicemia. Approximately half of all patients who receive chemotherapy develop such severe oral mucositis that becomes dose-limiting such that the patient's cancer treatment must be modified, compromising the prognosis.

The present invention provides a composition comprising Halobacteria extracts. Halobacteria are recognized as archaea, rather than bacteria. The name 'Halobacteria' was assigned to this group of organisms before the existence of the domain Archaea was realized, and remains valid according to taxonomic rules. In a non-taxonomic context, halophilic archaea are also sometimes referred to as Haloarchaea to distinguish them from halophilic bacteria.

The composition comprises Archaebacteria DN-1 which is known also as DN-1—homogenate of Halobacteria. The DN-1 homogenate contains two groups of antioxidants—water soluble and oil soluble, so it is an antioxidant containing extract with wide-ranging effects on body restoration after radiation, wounds, burns, pressure sores and scarring after surgery. The antioxidant promotes and increase mortality and further extends the life span. There are several ways to measure antioxidants activity. The oxygen radical absorbance capacity (ORAC) is the current industry standard for assessing antioxidant strength of whole foods, juices and food additives. Other measurement tests include the Folin-Ciocalteu reagent, and the Trolox equivalent antioxidant capacity assay The Halobacteria extracts composition of the present invention have the ability to both enhance and strengthen the human immune system. The composition further increases the body's natural resistance system, increases the body's capacity to withstand a successful bacterial and/or viral invasion, and boosts the body's ability to recuperate.

This formulation also provides effective blood purification and detoxification.

The product may be obtained in the following manner: the bacterial mass obtained from the culture of archaebacteria is first dispersed in a salt solution solvent to form a solution; the solution is then incubated for about 2 weeks at about 42°; following incubation the solution is centrifuged yielding a sediment. The isolated sediment layer is re-suspended isolated to form a solution. The centrifugation, isolating the sediment and re-suspending is repeated twice. The formed solution after these steps is sonicated for three times. The sonicated solution is centrifuged, yielding a sediment, wherein said sediment is, Halobacteria homogenate, Archaebacteria DN1.

The method for extracting the product according to the invention is applied to archaebacteria, preferably to Halobacteria, and more particularly to *Halobacterium halobium*.

The composition of the present invention may further comprises *Dunaliella* extracts.

The combination of Halobacteria extracts with *Dunaliella* extract further provides antioxidant activity and therefore increases the useful of the treatment of skin damages resulting from radiation, surgery or any drug treatment (such as scars, burns, bedsores and mucositis).

The *Dunaliella*, a halotolerant green alga, accumulate high concentration of β-carotene when grown under defined condition. *Dunaliella* possess the ability to accumulate very large amounts of β-carotene (more than 10% of the algae dry weight) under defined condition. The extent of β-carotene accumulation was shown to have a direct function of the integral amount of light and high NaCl concentration to which the algae are exposed during a division cycle.

β-carotene possesses powerful anti-cancer properties. By reducing the amount of harmful free radicals in the body that can otherwise damage the DNA which further promotes cosmetic-related problems such as wrinkles and, on a more serious note, it can increase a subject risk of cancer. *Dunaliella* known to have a direct influence on the immune cells. *Dunaliella* further contains another carotenoid called zeaxanthin, a valuable antioxidant with the ability to both help prevent and treat debilitating condition that causes progressive vision loss.

The term 'about' hereinafter refers to a range of 25% below or above a quoted value.

Reference is now made to an embodiment of the present invention disclosing a topical composition for treating skin damage comprising: (a) Halobacteria extracts comprising strong antioxidants with high redox potential; said strong antioxidants inhibiting known oxidative mechanisms correlated with skin damage; and (b) *Dunaliella* extracts for reducing the amount of free radicals in skin damage;

wherein said topical composition has synergistic anti-inflammatory effect, defined by attenuation of at least of Il-1β or TNF-α induction on said inflamed skin as compared to an untreated control skin.

Reference is now made to an embodiment of the present invention disclosing the composition mentioned above, wherein said Halobacteria extract is Halobacteria homogenate, Archaebacteria DN1, and said Archaebacteria DN-1 has an anti-oxidant activity substantially correlated with a body serum total antioxidant capacity (TAC) of at least 167.1 μMol Trolox Equivalent/100 g; said anti-oxidant activity measured at the treatment site by at least one assay selected from a group consisting of:
  i. Assay 1—oxygen radical absorbent capacity (ORAC);
  ii. Assay 2—of ferric reducing ability of plasma (FRAP);
  iii. Assay 3—of 2,2-diphenyl-1-picrylhydrazyl (DPPH);
  iv. Assay 4—of 3-ethyl-benzothiazoline-6-sulfonic acid (ABTS);
  v. Assay 5—of Trolox Equivalent Antioxidant Capacity (TEAC); and
    any combination thereof.

Reference is now made to an embodiment of the present invention disclosing the composition mentioned above, wherein said body serum measurement is taken from any body site.

Reference is now made to an embodiment of the present invention disclosing the composition mentioned above, wherein said Assays 1-5 measurement of total antioxidant activity is performed in a serum sample of said composition.

Reference is now made to an embodiment of the present invention disclosing the composition mentioned above, wherein said Halobacteria extracts configured to actuate (a) antioxidant and redox potential to a wound site, correlated with an increase in erythrocytes (RBC), leukocytes (WBC), Interleukin-6 (IL-6) concentration and glutathione concentration in a treated subject compared with an untreated control; and (b) protection of membranes from oxidation by reacting with radicals produced in the chain reaction.

Reference is now made to an embodiment of the present invention disclosing the composition mentioned above, wherein said composition is configured to affect one selected from a group consisting of: (a) decreasing of clinical syndromes resulting from radiation in variety of systems such as the nerve system, digesting system and vascular system; (b) treating cardiac, liver or vascular diseases, stabilization and improvement of the immune system and the endocrine system; and any combination thereof.

Reference is now made to an embodiment of the present invention disclosing the composition mentioned above, wherein said composition comprises by weight, -2.5% 10% Archaebacteria DN-1.

Reference is now made to an embodiment of the present invention disclosing the composition mentioned above, wherein said topical composition is selected from the group consisting of: a gel, a milk, a lotion, a serum, a mask, ointments or a cream.

Reference is now made to an embodiment of the present invention disclosing the composition mentioned above, wherein said skin damage is selected from the group consisting of: skin blemish, scars, burns, mucositis or/and bedsores resulting from radiation treatment, surgery or any drug treatment.

Reference is now made to an embodiment of the present invention disclosing the composition mentioned above, wherein said composition promotes rehabilitation of the body tissue after radiation comprising at least one selected from a group consisting of alleviation of depression, reduction of clinical syndromes resulting from radiation, treatment of cardiac, liver or vascular diseases, stabilization and improvement of the immune system and the endocrine system and any combination thereof.

Reference is now made to an embodiment of the present invention disclosing the composition mentioned above, wherein said composition further comprises preservatives, surfactants, humectants, emulsifiers, thickening agents, perfumes, preservatives, vegetable or mineral oils, antiseptic agents, acidifying or alkalinizing agents, vitamins, anti-UV agents, solvents, pH-stabilizing agents, silicones and combination thereof.

Reference is now made to an embodiment of the present invention disclosing a method of producing a topical composition for treating skin damage comprising the steps of: (a) obtaining Halobacteria extracts comprising strong antioxidants with high redox potential; said strong antioxidants inhibiting known oxidative mechanisms correlated with skin damage; (b) obtaining *Dunaliella* extracts for reducing the amount of free radicals in skin damage; and (c) mixing said Halobacteria extracts and *Dunaliella* extracts; wherein said topical composition has synergistic anti-inflammatory effect, defined by attenuation of at least of Il-1β or TNF-α induction on said inflamed skin as compared to an untreated control skin.

Reference is now made to an embodiment of the present invention disclosing the method mentioned above, wherein said Halobacteria extract is Halobacteria homogenate, Archaebacteria DN1, and producing of said Archaebacteria DN1 comprising the steps of: (a) obtaining a bacterial mass by culturing Halobacteria; (b) dispersing a quantity of the bacterial mass in a salt solution solvent to form a solution; (c) incubating the solution for about 2 weeks at about 42° C.; (d) centrifuging solution of (c), yielding a sediment; (e) re-suspending isolated sediment layer of (d) to form a solution; (f) repeating (d) and (e) twice to form a solution; (g) sonicating solution of (f) three times; (h) centrifuging of sonicated solution of (g), yielding a sediment; wherein said sediment of (h), Halobacteria homogenate, is Archaebacteria DN1, having an anti-oxidant activity which has a wide range impact on rehabilitation of the skin tissue after radiation; said activity substantially correlated with a body serum TAC of at least 167.1 μMol Trolox Equivalent/100 g at the treatment site; said anti-oxidant activity measured at the treatment site by at least one assay selected from a group consisting of:
  i. Assay 1—oxygen radical absorbent capacity (ORAC);
  ii. Assay 2—of ferric reducing ability of plasma (FRAP);
  iii. Assay 3—of 2,2-diphenyl-1-picrylhydrazyl (DPPH);
  iv. Assay 4—of 3-ethyl-benzothiazoline-6-sulfonic acid (ABTS);
  v. Assay 5—of Trolox Equivalent Antioxidant Capacity (TEAC); and
    any combination thereof.

Reference is now made to an embodiment of the present invention disclosing the method mentioned above, wherein said solvent comprises salt solution and at least one of a group comprising peptone, yeast extract, casein, and any combination thereof.

Reference is now made to an embodiment of the present invention disclosing the method mentioned above, wherein said composition is for one selected from a group consisting of: (a) decreasing of clinical syndromes resulting from radiation in variety of systems such as the nerve system, digesting system and vascular system; (b) treating cardiac, liver or vascular diseases, stabilization and improvement of the immune system and the endocrine system; and any combination thereof.

Reference is now made to an embodiment of the present invention disclosing the method mentioned above, wherein said composition comprises:
 i. by weight, 10%-2.5% Archaebacteria DN-1;
 ii. preservatives, surfactants, humectants, emulsifiers, thickening agents, perfumes, preservatives, vegetable or mineral oils, antiseptic agents, acidifying or alkalinizing agents, vitamins, anti-UV agents, solvents, pH-stabilizing agents, silicones; and any combination thereof.

Reference is now made to an embodiment of the present invention disclosing the method mentioned above, wherein the composition: (a) treats skin blemish such as scars, burns or/and bedsores resulting from radiation, surgery or any drug treatment; (b) promotes rehabilitation of the body tissue after radiation, alleviation of depression, reduction of clinical syndromes resulting from radiation, treatment of cardiac, liver or vascular diseases, stabilization and improvement of the immune system and the endocrine system; and any combination thereof.

Reference is now made to an embodiment of the present invention disclosing the method mentioned above, wherein said Halobacteria extract has antioxidant activity due to its redox properties, resulting in increment of erythrocytes (RBC), leukocytes (WBC), Interleukin-6 (IL-6) concentration and glutathione concentration

EXAMPLES

Halobacteria and *Dunaliella* extracts are known to have beneficial effects on human skin. A new formulation made of a mixture of these two extracts (Synergy) had been developed and needs to be tested for efficacy, compared against the individual extracts. Previous evaluation of Synergy in the ex-vivo human skin model showed that low concentration of the test item were well tolerated, although lack a significant effect in both inflammatory skin model and UV protection. It was assumed that the concentration of the tested Synergy formulation was lower than its effective one. To overcome this issue, a new formulation of Synergy was prepared, and the study was started with dose response and composition optimization experiments in order to determine the most effective Synergy formulation. In addition, the extract was tested on new model systems to evaluate their impact on human keratinocytes and skin cell lines.

The present procedure is applicable to the extraction of Halobacteria. It is based on the weakness of the cell envelopes of these microorganisms when they are exposed to low concentrations of salts, for example, in fresh water; under these conditions the cells of halophilic bacteria lyse (rupture), releasing all the cell components into the medium.

The following examples are intended to illustrate the present invention without, however, being of a limiting nature:

The present invention discloses the effect of extracts of Halobacteria, *Dunaliella* and synergy between them in the ex-vivo human skin and keracinocytes cell lines models.

Ex-Vivo Human Skin Platform
Skin Culturing
The human skin organ cultures were obtained from healthy 45-51 years old females undergoing plastic surgery. The study was initiated the day of surgery.

Fixed size ex-plant skin pieces (0.64 cm2) were cut from the skin tissue (abdominal), using a designated press apparatus. The skin pieces were laid in 6-well culture plates containing skin culture medium (DMEM supplemented with antibiotics), dermal side down in the medium and epidermis up. The pieces were incubated overnight at 37° C. with 5% $CO_2$ for recovery.

Protection Against UV
The skin pieces were prepared as mention above (see skin culturing section).

After the recovery, the viability and the extent of apoptosis in the epidermis layer were measured using MTT and Caspase 3 assays, respectively.

The UVB protection test was initiated by topically applying the tested extracts (Halobacteria, *Dunaliella* and Synergy; 3 uL) on the skin. Each well contained three skin pieces (2 wells*3 pieces per each treatment). Pieces w/o any treatment and with the vehicle (7.5% NaCl) were used as negative controls.

The pieces were incubated at 37° C. with 5% $CO_2$.

On the next day, the tested groups were washed with PBS and were exposed to 300 mJoule of UVB light radiation. Immediately after the exposure, the PBS was replaced with 2 mL of fresh skin culture medium. Pieces with extracts not exposed to UV light used as untreated control. The culture medium was refreshed in all the control groups.

The pieces were incubated overnight at 37° C. with 5% $CO_2$.

The epidermis was peeled from all skin pieces. The viability and the extent of apoptosis in the epidermis were measured by using MTT and Caspase 3 assays.

Anti-Inflammatory Activity
The skin pieces were prepared as mention above (see skin culturing section).

After recovery, the viability in the epidermis was assessed by MTT assay.

For induction of inflammatory characteristics, fresh skin culture medium was supplemented with a combination of EGF (2.5 ng/ml) and LPS (10 µg/mL), and was added to the appropriate wells according to Table 1. Fresh skin culture medium without supplements was used as negative, untreated control. Fresh skin culture medium in the absence of the three extract was used as negative, baseline control. Cultures stimulated with LPS and EGF were treated with the tested extracts (Halobacteria, *Dunaliella* and Synergy) by applying them on the epidermis topically (3 uL). The positive control contained LPS and EGF, with no addition of treatment agent.

The pieces were incubated for 48 hrs at 37° C. with 5% $CO_2$.

Each treatment was carried out in triplicates when each well contains two skin pieces (3 well*2 pieces per each group).

After the incubation, the spent medium from treated skin cultures was collected under standardized conditions (~1000 µl) and centrifuged at 14,000 g for 5 min to remove particulates. The clear supernatants were frozen at −70° C. for ELISA analysis.

The epidermis was peeled from all the skin pieces and the viability measured by MTT assay.

The contents of the cytokines TNFα, IL-1β and IL-6 in the skin culture supernatants were analyzed using appropriate kits according to manufacturer instructions. Cytokine calibration curve were generated in duplicates. Each sample was tested in duplicates.

Human Keratinocyte Cells Platform

This part of the experiment was carried out in a certified HaCaT cell line (an immortal human keratinocyte line) purchase from CLS GmbH.

The aim of this experiment was to evaluate the direct effect of the tested extracts on human skin cells, without the need to penetrate into the skin layers using the cytotoxicity assay measurements. A differential effect of the isolated cells vs. the skin may point that the extract does not penetrate the epidermis.

Results

Skin—Protection Against UVB Irradiation

Figure 2:
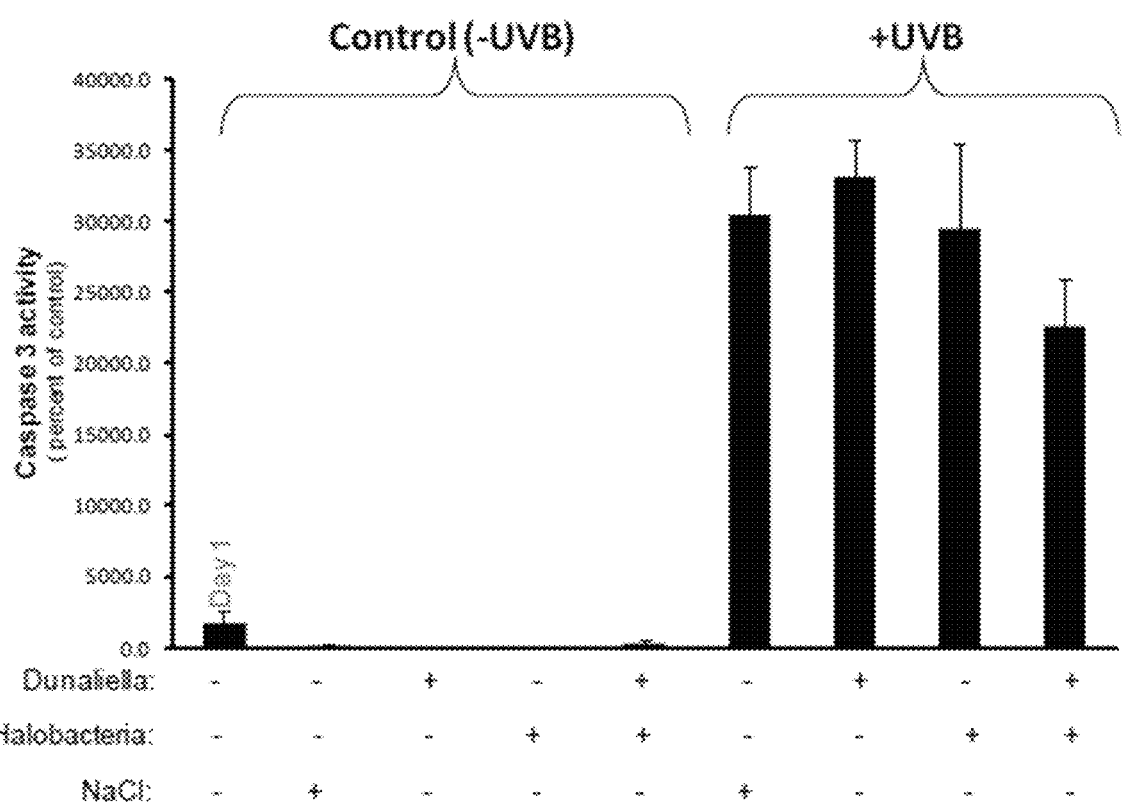
FIG. 2 presents a graph of Caspase 3 assay results of the different treatment groups without or with UVB radiation, in accordance with a preferred embodiment of the present invention. Apoptosis was measured by Caspase-3 assay. Results are shown as percent of control. Mean±SEM, n=3,4.

Ex-vivo human skin organ cultures were treated without or with Dunaliella and Halobacteria extracts. Samples were then exposed to 300 mJ UVB irradiation. Viability was tested by the MTT assay. The different extracts did not compromise human skin viability as shown in FIG. 1. Also, apoptosis was measured by Caspase3 assay. No significant effect of Halobacteria and Dunaliella extracts on UVB-induced damage as shown in FIG. 2.

Skin—Anti-Inflammatory Activity

Inflammation of ex-vivo human skin organ cultures was induced by LPS & EGF and treated without or with Dunaliella (0.69 mg/cm2) Halobacteria (2.76 mg/cm2) extracts (20:80 ratio) or both.

Figure 3:
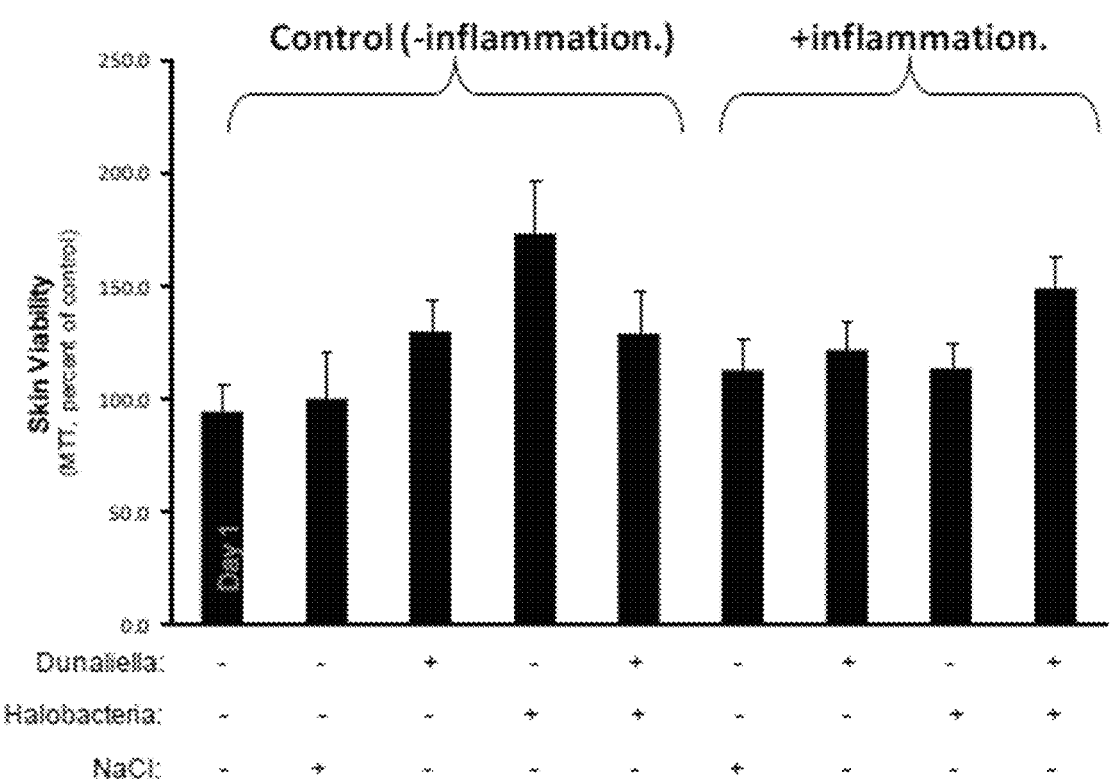
FIG. 3 present a graph of MTT assay results after of the different treatment groups without or with the induction of inflammation, in accordance with a preferred embodiment of the present invention. Inflammation in HSOC was induced by LPS/EGF treatment. The, HSOC were incubated without or with 20% *Dunaliella* (0.69 mg/cm$^2$) or halobacteria (2.76 mg/cm$^2$) or both for 24 hrs and exposed to 300 mJ UVB irradiation. Epidermis viability was then measured by MTT assay. Results are shown as percent of control. Mean±SEM, n=3,4. Results show that the different extracts did not comprise human skin viability.

The different extracts did not compromise human skin viability as shown in FIG. 3.

Figure 4:
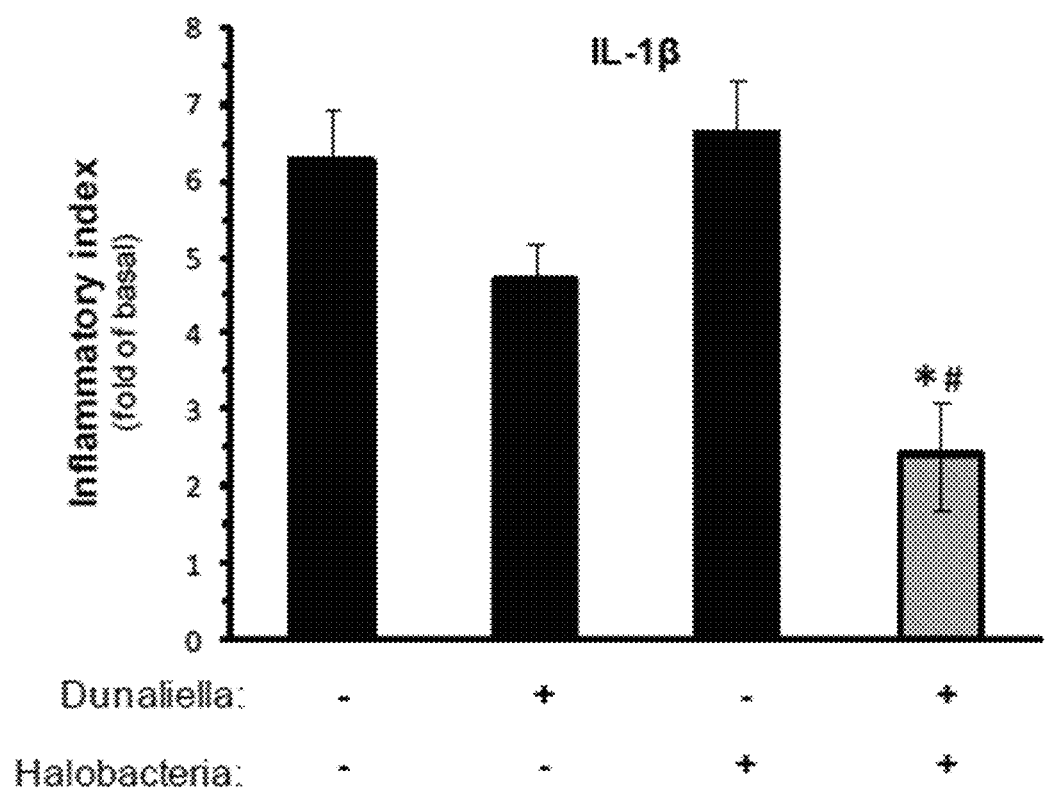
FIG. 4 present a graph of quantitative ELISA results for IL-1β after skin treated by the extracts and exposed to inflammatory inducers, in accordance with a preferred embodiment of the present invention. The levels of secreted IL-1β were measured by ELISA, according to manufacturer instructions. Results are shown as fold of basal secretion. Mean±SEM, n=4-6. *<0.05 for difference from untreated control; #p<0.05 for difference from the additive effects of Dunaliella- and halobacteria-treated cells. Results show synergy attenuated IL-1β induction in inflamed skin.
Figure 5:
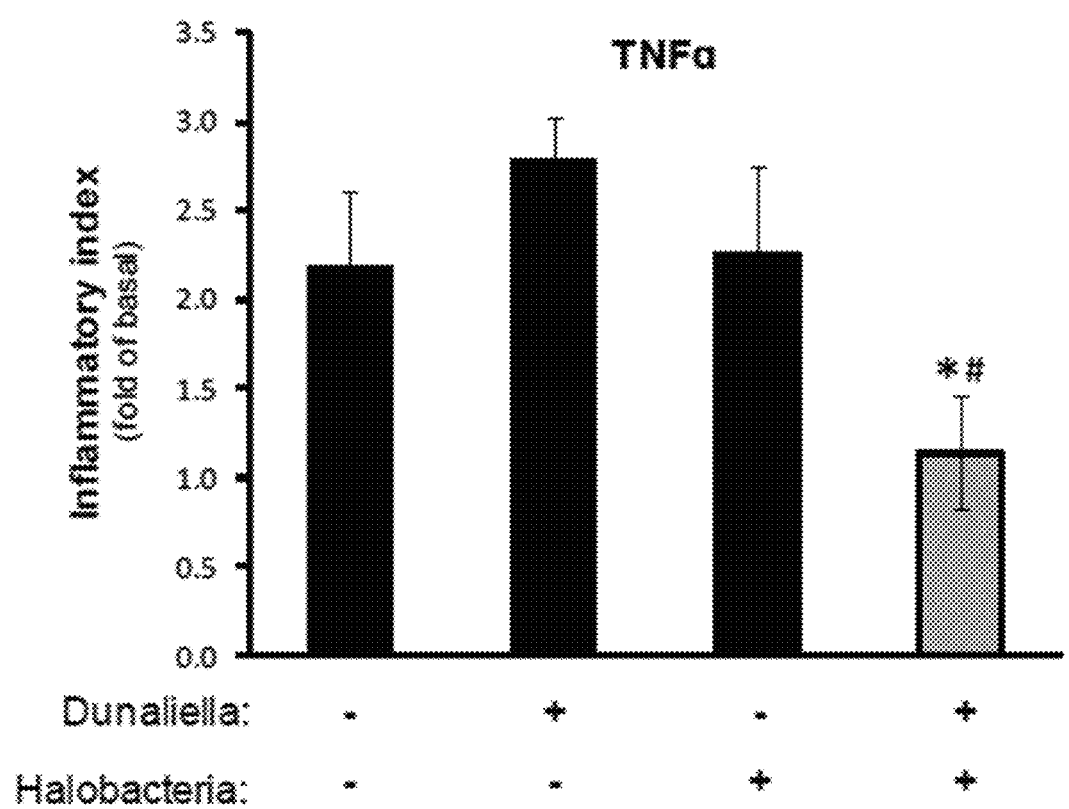
FIG. 5 presents a graph of quantitative ELISA results for TNFα after skin treated by the extracts and exposed to inflammatory inducers, in accordance with a preferred embodiment of the present invention. The levels of secreted TNFα were measured by ELISA, according to manufacturer instructions. Results are shown as fold of basal secretion. Mean±SEM, n=5-6. *<0.05 for difference from untreated control; #p<0.05 for difference from the additive effects of Dunaliella- and halobacteria-treated cells. Results show synergy attenuated TNFα induction in inflamed skin.
Figure 6:
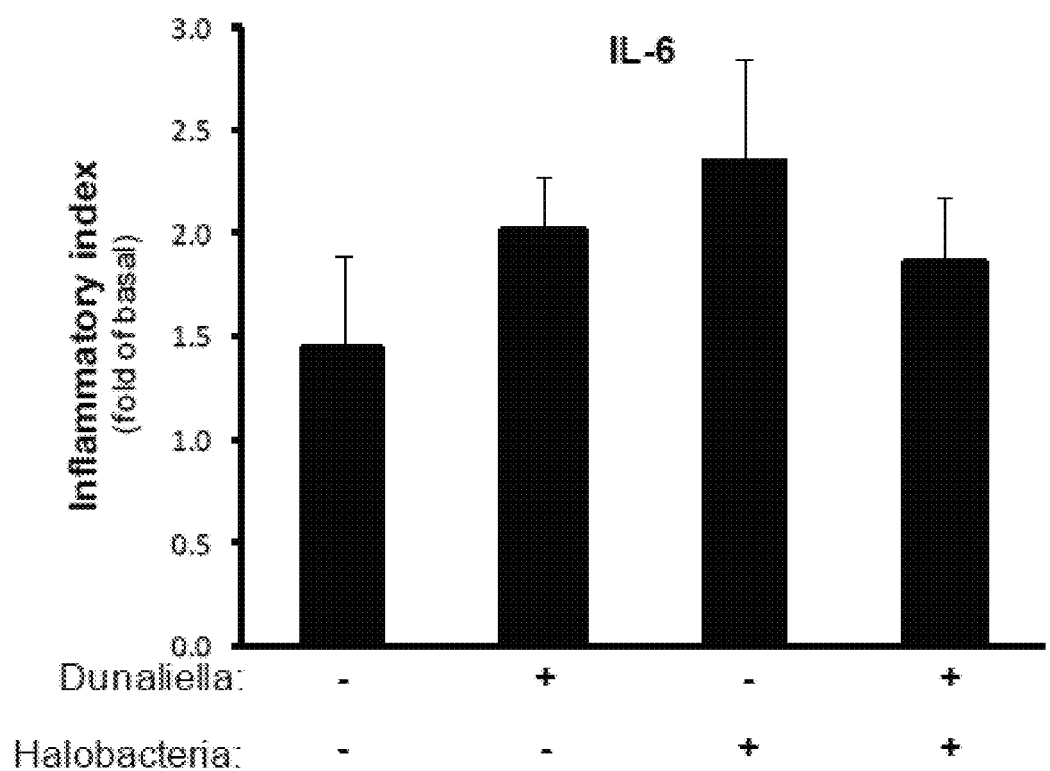
FIG. 6 presents a graph of quantitative ELISA results for IL-6 after skin treated by the extracts and exposed to inflammatory inducers, in accordance with a preferred embodiment of the present invention. The levels of secreted IL-6 were measured by ELISA, according to manufacturer instructions. Results are shown as fold of basal secretion. Mean±SEM, n=5-6. Results show lack of attenuating effect of synergy on IL-6 induction in inflamed skin.

Combination of Dunaliella (20%) and Halobacteria (80%) synergistically attenuate LPS/EGF-induced inflammation in human skin as shown in the quantitative ELISA results for IL-1β after skin treated by the extracts and exposed to inflammatory inducers in FIG. 4. The Synergy attenuated IL-1β induction in inflamed skins. Quantitative ELISA results for TNFα after skin treated by the extracts and exposed to inflammatory inducers are shown in FIG. 5. The Synergy attenuated TNFα induction in inflamed skins. Quantitative ELISA results for IL-6 after skin treated by the extracts and exposed to inflammatory inducers are shown in FIG. 6. The Synergy did not attenuate the induction of IL-6 in inflamed skins.

Human Keratinocyte Cells—Dose Response and Synergy Composition

Figure 7:
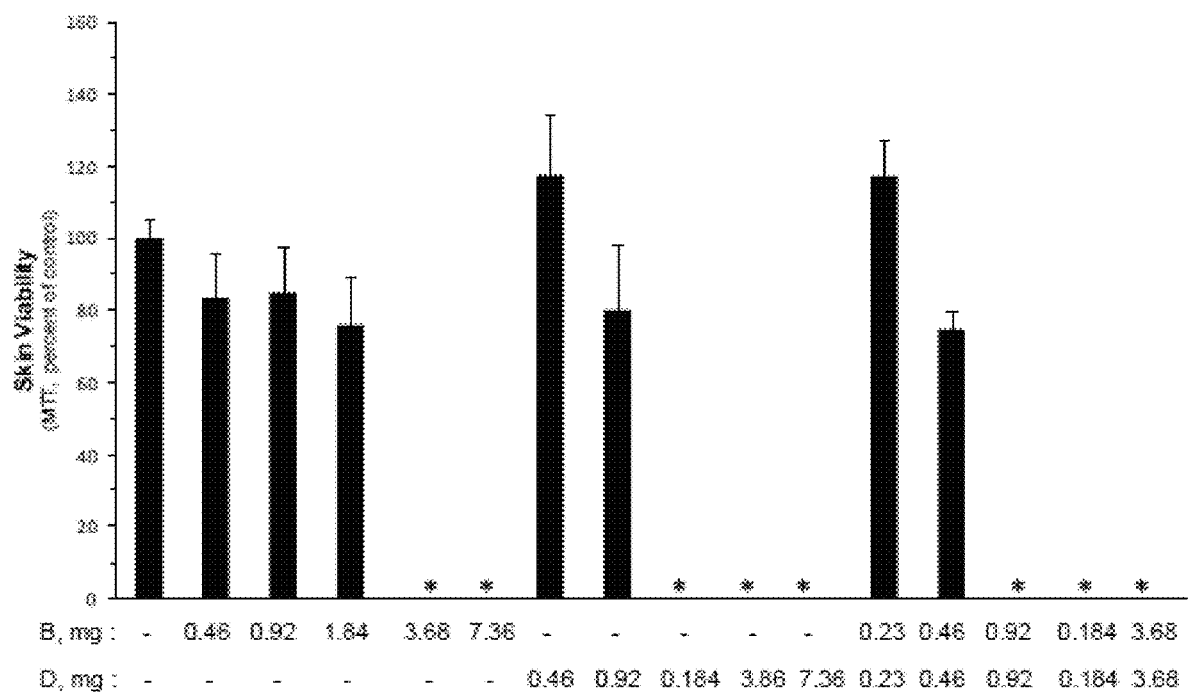
FIG. 7 presents a graph of MTT assay results of keratinocyte cells exposed to Dunaliella, Halobacteria and Synergy extracts, in accordance with a preferred embodiment of the present invention. HaCaT cells were incubated without or with the indicated concentrations of Dunaliella, Halobacteria and Synergy extracts for 24 hrs. Cell viability was measured by MTT assay. Results are shown as percent of control. Mean±SEM, n=5-6. Results show dose-response analysis of the extracts on keranocytes viability.
Figure 8:
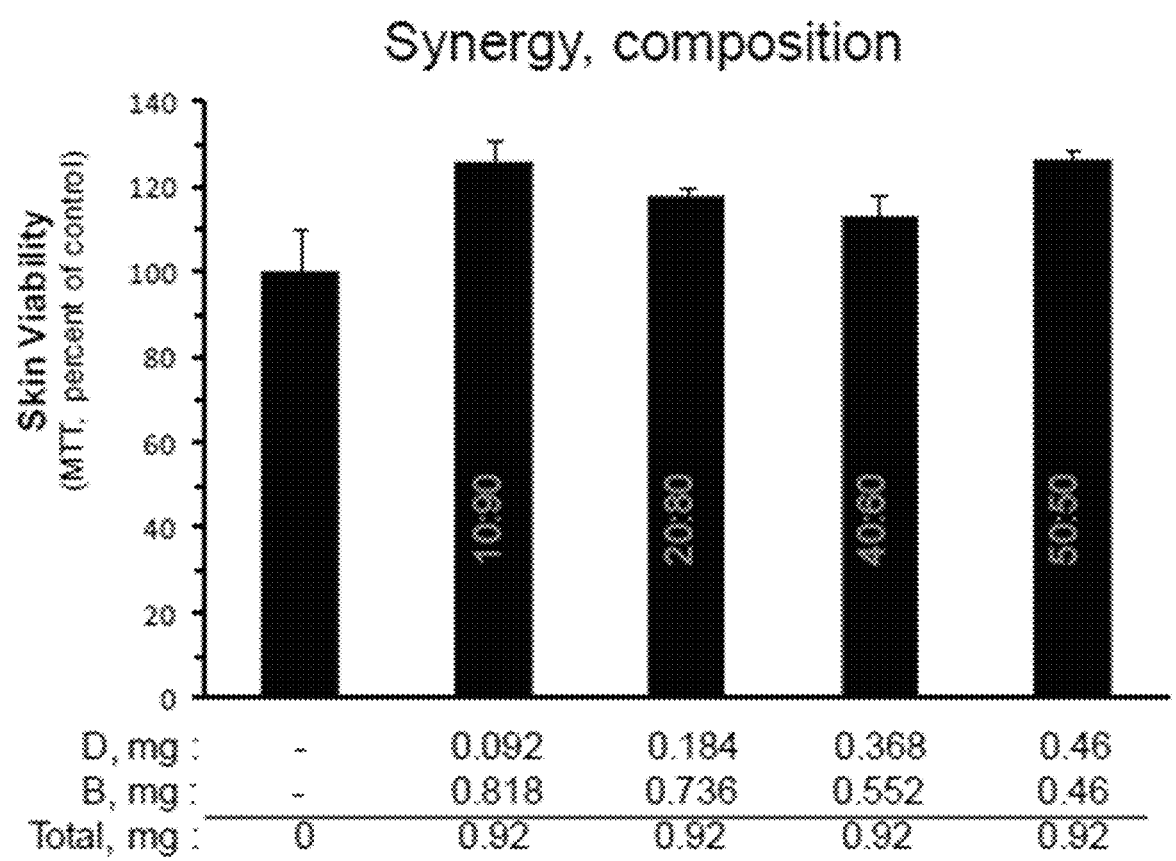
FIG. 8 presents a graph of MTT assay results after keratinocyte cells exposed to different ratios of Dunaliella and Halobacteria, in accordance with a preferred embodiment of the present invention. HaCaT cells were incubated without or with the indicated concentrations of Dunaliella, Halobacteria and Synergy extracts for 24 hrs. Cell viability was measured by MTT assay. Results are shown as percent of control. Mean±SEM, n=4-5.

Dose response analyses of the effect of Dunaliella and Halobacteria extract on keratinocytes cell-line viability. MTT assay results of keratinocyte cells exposed to Dunaliella, Halobacteria and Synergy extracts are shown in FIG. 7. MTT assay results after keratinocyte cells exposed to different ratios of Dunaliella and Halobacteria are shown in FIG. 8.

CONCLUSIONS

Protection from UVB-induced damage: we disclosed the ability of the compounds to protect against UV-induced damage. As shown in FIG. 1, the epidermis viability in all groups was not decreased below the basic level as measured on day 1. After the topical application of the three compounds, the samples were irradiated at 300 mJoule (moderate to high radiation). In the control sample, a clear and significant increase in apoptosis (measured by caspase 3 activation) was demonstrated (FIG. 2). Both Dunaliella and Halobacteria extracts had no noticeable protective effect. Although Synergy had reduced caspase 3 activity by 25%, it failed to reach significance.

Anti-Inflammatory activity: the anti-inflammatory activity of Dunaliella, Halobacteria and synergy on human skin was disclosed. Skin inflammation was induced according to standard methodology by the combination of EGF and LPS. As shown in FIG. 3, the viability of the epidermis was not altered. FIG. 4, 5, 6) shows that inflammatory index (calculated by the fold increase of the cytokines) was significantly reduced by synergy. Specifically, synergy at Dunaliella (20): Halobacteria (80) ratio reduce IL-1β and TNFα induction in the inflamed skins. However, IL-6 levels have not altered by the different extracts. Interestingly, IL-1β and TNFα have been reported to be key factors in inflamed skin diseases such as psoriasis and atopic dermatitis. In addition, newly developed biological drugs against these two cytokines (antibodies) are now been evaluated by the FDA. Therefore, the potential beneficial effect of synergy in these diseases is promising.

Dose-response analysis in human keratinocytes cell culture: evaluation of the direct effect of the tested extracts on human skin cells was disclosed, without the need to penetrate into the skin layers using the cytotoxicity assay measurements. The viability results obtained here vary from the results in the skin pieces; the different extracts reduced the cell viability in a dose-dependent manner (FIGS. 7-8). However, the results from the inflamed skin clearly demonstrate that the active compound can penetrate the stratum corneum barrier and interact in the target area.

Extraction of Halobacteria Homogenate DN-1.

Extraction Halobacteria homogenate DN-1 obtained from Halobacterium halobium, preparing a salt stock solution: Adding 240 g/L of NaCl, 30 g/L of $MgCL_2*6H_2O$, 35 g/L of $MgSO_4*7H_2O$, 7 g/L KCl to a flask. Adding pure water to near the final required volume of the same flask. The salt then dissolved using a magnetic stirrer.

Adding 15 ml $CaCl_2*2H_2O$

Adjusting the PH of the flask solution up to 7 by using 1M TrisCl buffer.

Transferring the above solution to a graduated cylinder and toping up with water to the exact final volume.

A quantity of bacterial mass (5 gram) is dispersed beforehand and been added to the solution described below:

Adding 767 ml from the above salt stock solution, 200 ml of pure water, 5 g of peptone, 1 g of yeast extract, and 1 g of Casein.

Adjusting the volume with 1000 ml of pure water.

Incubating the culture for sufficient time and temperature to 42° C.

Suspending the culture for about two weeks

At the end of the two-week phase, four portions of 50 ml each, are transferred to clean containers and centrifuged.

Centrifugation of the 2 weeks old culture for 7500 RPM, at 4° C. for 15 minutes, yielding a sediment Isolating the sediment and re-suspending it within a solution of 2M NaCl+0.15M $MgCl_2$.

Centrifugation of the solution is performed for 7500 RPM, at 4° C., for additional 15 minutes, yielding a sediment Isolating the sediment layer and re-suspending it within a solution of 7.5% NaCl.

Sonicating the above solution three times each time for 30 sec in 15 ml containers. In between each time cooling the solution in an ice bath until a different is shown in the color and turbidity or transparency of the solution Centrifugation of the solution is performed yielding separation fractions (the centrifugation procedure is performed in 7500 RPM at 4° C. for 10 min). The resulting sediment is isolated and kept in (−4°) C.

Homogenate from red Halobacteria-Archea and microalgae *Dunaliella* isolated in 7.5% NaCl and pH=7

Mixing of:

375 gram NaCl 75 ml of above homogenate

Water is added to reach an exact volume of 5 L

The *Dunaliella* solution is added to the Halobacteria solution to reach a proportion of 80% Halobacteria DN-1 extract and 20% *Dunaliella* extract*.

**Dunaliella* extract is purchased from a certified supplier.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A topical composition for treating skin damage comprising
   a. Halobacteria sediment extracts, said Halobacteria sediment extracts comprise strong antioxidants with high redox potential and inhibiting known oxidative mechanisms correlated with skin damage; and
   b. *Dunaliella* extracts for reducing the amount of free radicals in skin damage;
   wherein said Halobacteria sediment extracts and said *Dunaliella* extracts are at a ratio of 80:20 Halobacteria and *Dunaliella* and have a synergistic anti-inflammatory effect, defined by attenuation of cytokine at least of IL-1β or TNF-α induction on said inflamed skin as compared to an untreated control skin.

2. The composition according to claim 1, wherein said Halobacteria sediment extracts is Halobacteria homogenate Archaebacteria DN-1, and said Archaebacteria DN-1 has an anti-oxidant activity substantially correlated with a body serum total antioxidant capacity (TAC) of at least 167.1 µMol Trolox Equivalent/100 g; said anti-oxidant activity measured at the treatment site by at least one assay selected from the group consisting of:
   i. Assay 1—oxygen radical absorbent capacity (ORAC);
   ii. Assay 2—of ferric reducing ability of plasma (FRAP);
   iii. Assay 3—of 2,2-diphenyl-1-picrylhydrazyl (DPPH);
   iv. Assay 4—of 3-ethyl-benzothiazoline-6-sulfonic acid (ABTS);
   v. Assay 5—of Trolox Equivalent Antioxidant Capacity (TEAC); and
   any combination thereof.

3. The composition according to claim 2, wherein said body serum measurement is taken from any body site.

4. The composition according to claim 2, wherein said Assays 1-5 measurement of total antioxidant activity is performed in a serum sample of said composition.

5. The composition according to claim 1, wherein said Halobacteria sediment extracts configured to actuate:
   a. antioxidant and redox potential to a wound site, correlated with an increase in erythrocytes (RBC), leukocytes (WBC), Interleukin-6 (IL-6) concentration and glutathione concentration in a treated subject compared with an untreated control;
   b. protection of membranes from oxidation by reacting with radicals produced in the chain reaction.

6. The composition according to claim 1, further wherein said composition is configured to affect one selected from a group consisting of:
   a. decreasing of clinical syndromes resulting from radiation in variety of systems such as the nerve system, digesting system and vascular system;
   b. treating cardiac, liver or vascular diseases, stabilization and improvement of the immune system and the endocrine system; and
   any combination thereof.

7. The composition according to claim 1, wherein said composition comprises by weight, 10%-2.5% Archaebacteria DN-1.

8. The composition according to claim 1, wherein said topical composition is selected from the group consisting of: a gel, a milk, a lotion, a serum, a mask, ointments or a cream.

9. The composition according to claim 1, wherein said skin damage is selected from the group consisting of: skin blemish, scars, burns, mucositis or/and bedsores resulting from radiation treatment, surgery or any drug treatment.

10. The composition according to claim 1, wherein said composition promotes rehabilitation of the body tissue after radiation comprising at least one selected selected form a group consisting of alleviation of depression, reduction of clinical syndromes resulting from radiation, treatment of cardiac, liver or vascular diseases, stabilization and improvement of the immune system and the endocrine system and any combination thereof.

11. The composition according to claim 1, wherein said composition further comprises at least one additional component, said component selected from a group consisting of preservatives, surfactants, humectants, emulsifiers, thickening agents, perfumes, preservatives, vegetable or mineral oils, antiseptic agents, acidifying or alkalinizing agents, vitamins, anti-UV agents, solvents, pH-stabilizing agents, silicones and combination thereof.

12. A method of producing a topical composition for treating skin damage comprising steps of:
   a. Obtaining a Halobacteria sediment extracts; and
   b. Obtaining a *Dunaliella* extract for reducing the amount of free radicals in skin damage;
   c. mixing said Halobacteria sediment extracts and *Dunaliella* extracts;
   wherein said Halobacteria sediment extracts comprise strong antioxidants with high redox potential; said strong antioxidants inhibiting known oxidative mechanisms correlated with skin damage said topical composition has synergistic anti-inflammatory effect, defined by attenuation of at least of Il-1β or TNF-α induction on said inflamed skin as compared to an untreated control skin.

13. The method of 12, wherein said Halobacteria sediment extracts is Halobacteria homogenate Archaebacteria DN1, and producing of said Archaebacteria DN1 comprising the steps of:
   a. obtaining a bacterial mass by culturing Halobacteria;
   b. dispersing a quantity of the bacterial mass in a salt solution solvent to form a solution;
   c. incubating the solution for about 2 weeks at about 42° C.;

d. centrifuging solution of (c), yielding a sediment;
e. re-suspending isolated sediment layer of (d) to form a solution
f. repeating (d) and (e) twice to form a solution
g. sonicating solution of (f) three times
h. centrifuging of sonicated solution of (g), yielding a sediment
wherein said sediment of (h), Halobacteria homogenate, is Archaebacteria DN1, having an anti-oxidant activity which has a wide range impact on rehabilitation of the skin tissue after radiation; said activity substantially correlated with a body serum TAC of at least 167.1 µMol Trolox Equivalent/100 g at the treatment site; said anti-oxidant activity measured at the treatment site by at least one assay selected from a group consisting of:
i. Assay 1—of oxygen radical absorbent capacity (ORAC);
ii. Assay 2—of ferric reducing ability of plasma (FRAP);
iii. Assay 3—of 2,2-diphenyl-1-picrylhydrazyl (DPPH);
iv. Assay 4—of 3-ethyl-benzothiazoline-6-sulfonic acid (ABTS);
v. Assay 5—of Trolox Equivalent Antioxidant Capacity (TEAC); and
any combination thereof.

14. The method of claim 12 wherein said solvent comprises salt solution and at least one of a group comprising peptone, yeast extract, casein and any combination thereof.

15. The method according to claim 12, further wherein said composition is for one selected from a group consisting of:
a. decreasing of clinical syndromes resulting from radiation in variety of systems such as the nerve system, digesting system and vascular system;
b. treating cardiac, liver or vascular diseases, stabilization and improvement of the immune system and the endocrine system; and
c. any combination thereof.

16. The method according to claim 12, wherein said composition comprises:
a. by weight, 10%-2.5% Archaebacteria DN-1;
b. preservatives, surfactants, humectants, emulsifiers, thickening agents, perfumes, preservatives, vegetable or mineral oils, antiseptic agents, acidifying or alkalinizing agents, vitamins, anti-UV agents, solvents, pH-stabilizing agents, silicones; and
c. any combination thereof.

17. The method according to claim 12, wherein the composition:
a. treats skin blemish such as scars, burns or/and bedsores resulting from radiation, surgery or any drug treatment;
b. promotes rehabilitation of the body tissue after radiation, alleviation of depression, reduction of clinical syndromes resulting from radiation, treatment of cardiac, liver or vascular diseases, stabilization and improvement of the immune system and the endocrine system; and
c. any combination thereof.

18. The method according to claim 12, wherein said Halobacteria sediment extracts has antioxidant activity due to its redox properties, resulting in increment of erythrocytes (RBC), leukocytes (WBC), Interleukin-6 (IL-6) concentration and glutathione concentration.

* * * * *